(12) United States Patent
Voss et al.

(10) Patent No.: US 8,834,382 B2
(45) Date of Patent: Sep. 16, 2014

(54) METHOD FOR DETERMINING A CARDIAC FUNCTION

(75) Inventors: Gregory I. Voss, Solana Beach, CA (US); James M. Perry, Nashville, TN (US); Rankin A. Clinton, III, Franklin, TN (US); Bernhard B. Sterling, Danville, CA (US); Andrew R Lawrence, Eagan, MN (US)

(73) Assignee: Cardiac Profiles, Inc., Franklin, TN (US)

( * ) Notice: Subject to any disclaimer, the term of this patent is extended or adjusted under 35 U.S.C. 154(b) by 1634 days.

(21) Appl. No.: 12/011,122

(22) Filed: Jan. 23, 2008

(65) Prior Publication Data

US 2009/0187110 A1    Jul. 23, 2009

(51) Int. Cl.
*A61B 5/02* (2006.01)

(52) U.S. Cl.
USPC ............ 600/500; 600/501; 600/504; 600/506

(58) Field of Classification Search
None
See application file for complete search history.

(56) References Cited

U.S. PATENT DOCUMENTS

| 6,334,065 | B1 | 12/2001 | Al-Ali et al. |
| 6,503,206 | B1 | 1/2003 | Li et al. |
| 6,647,287 | B1* | 11/2003 | Peel et al. ..................... 600/513 |
| 6,898,452 | B2 | 5/2005 | Al-Ali et al. |
| 7,248,910 | B2 | 7/2007 | Li et al. |
| 2006/0173366 | A1 | 8/2006 | Hasegawa |
| 2007/0197924 | A1 | 8/2007 | O'Rourke |

FOREIGN PATENT DOCUMENTS

| EP | 07016759 | 11/2007 |
| WO | PCT/IL03/00586 | 1/2004 |

OTHER PUBLICATIONS

Hlimonenko et al., Assessment of Pulse Wave Velocity and Augmentation Index in different arteries in patients with severe coronary heart disease, 2007, Proc. 29th Annual Int. Conf. IEEE EMBS, Aug. 23-26, pp. 1703-1706.*

* cited by examiner

*Primary Examiner* — Benjamin P Blumel
(74) *Attorney, Agent, or Firm* — Steven R. Vosen

(57) ABSTRACT

A method for determining a cardiac function, comprising (i) determining base anatomical characteristics associated with the subject, (ii) determining pulse delay to a first body site ($PD_{01}$) and a second body site ($PD_{02}$) as a function of the anatomical characteristics, wherein the distance via the arterial tree from the aortic valve to the first body site ($PD_{01}$) is different than the arterial tree distance from the aortic valve to the second body site ($PD_{02}$), (iii) determining pulse wave velocity between the first body site and the second body site ($PWV_{12}$), (iv) determining pulse wave velocity between the aortic valve and the first body site ($PWV_{01}$) as a function of $PWV_{12}$, and the anatomical characteristics; and (v) determining the pre-ejection period (PEP) as a function of $PD_{01}$ and $PWV_{01}$.

19 Claims, 6 Drawing Sheets

PULSE WAVE VELOCITY

PRE EJECTION PERIOD

METHOD FOR DETERMINING A CARDIAC FUNCTION

FIELD OF THE PRESENT INVENTION

The present invention relates generally to methods of determining physiological characteristics associated with cardiac function. More specifically, the invention relates to improved methods for determining the pre-ejection period and pulse wave velocity.

BACKGROUND OF THE INVENTION

The study of the performance and properties of the physiology (including notably the cardiovascular system) of a living subject has proven useful for diagnosing and assessing any number of conditions or diseases within the subject. The performance of the cardiovascular system, particularly the heart, has characteristically been measured in terms of several pertinent parameters, such as pulse wave velocity, pulse transit time, stroke volume and cardiac output.

A key cardiovascular parameter (or physiological characteristic) is pulse wave velocity, i.e. the speed at which a pressure wave propagates throughout the arterial tree, or aortic pulse wave velocity, i.e. the speed at which a pressure wave propagates through the aorta or central arterial tree. As is well known in the art, pulse wave velocity measurements are often employed to evaluate the status of the cardiovascular system, particularly, the central arteries, e.g., as an index of large artery elasticity and stiffness. Pulse wave velocity measurements are also often employed to determine additional cardiovascular characteristics, such as stroke volume and cardiac output.

Arterial stiffness encompasses several properties, such as vascular distensibility, compliance and elastic modulus, and has been shown to be a good predictor of coronary heart disease and cardiovascular mortality. See, e.g., O'Rourke, et al., *Am J Hypertens*, vol. 15, pp. 426-444 (2002); Boutouyrie, et al., *Hypertension*, vol. 39, pp 10-15 (2002); Blacher, et al., *Circulation*, vol. 99, pp 2434-2439 (1999). In general, increased arterial stiffness can lead to increased systolic pressure, increased ventricular mass, and decreased diastolic coronary perfusion. Increased arterial stiffness has also been associated with reduced flow volume in the lower-extremity arteries. See e.g., Suzuki, et al., *Diabetes Care*, vol. 24, pp 2107-2114 (2001).

Various conventional methods, techniques and associated algorithms have been employed to determine pulse wave velocity. Illustrative are the methods described below.

Referring first to FIG. 1, there is shown a method for determining pulse wave velocity, which is commonly referred to as the "Frank" method. According to the "Frank" method, two pulse wave sensors (designated "$P_1$" and "$P_2$") are used to detect a pulse wave of the carotid artery and a pulse wave of the femoral artery. Distances "a" and "b+c" between the aortic valve region and respective pulse wave detection points are measured.

Referring to FIG. 2, the carotid artery pulse wave, which is obtained by the carotid artery pulse wave sensor ("$P_1$"), exhibits a waveform indicated by "a". The femoral artery pulse wave, which is obtained by the femoral artery pulse wave sensor ("$P_2$"), exhibits a waveform indicated by "b".

Predetermined rising times of the pulse waves, each of which correspond to a time when a level value reaches ⅕ of a peak value (designated "$RT_1$" and "$RT_2$"), are compared with each other to obtain a time difference between, i.e. time T. The pulse wave velocity (PWV) is then determined using a basic physics algorithm, i.e. velocity equals distance over time.

Referring now to FIGS. 3 and 4, there is shown a further method for determining pulse wave velocity, which is commonly referred to as a PWV original method. As illustrated in FIG. 3, according to this method, sensors are located in positions proximate the carotid and femoral arteries (designated "$P_3$" and "$P_4$", respectively) to detect pulse waves therein. In addition, a heart sound sensor (designated "HSS") is located proximate the aortic valve region. A straight distance "D" between the aortic valve region and the femoral artery pulse wave sensor ("$P_4$") is measured. Distance "D" is then multiplied by 1.3, i.e. a correction factor to provide actual arterial path.

There are several drawbacks and disadvantages associated with the Frank and PWV original methods. A major drawback is that it is generally more difficult to capture and maintain an accurate pulse wave signal via the noted methods.

Further methods and associated algorithms for determining pulse wave velocity are disclosed in McDonald, et al., "Left Ventricular Output Derived from the Time-Derivative and Phase Velocities of the Aortic Pressure Wave", *Medical and Biological Engineering*, vol. 11, pp. 678-690 (November 1973); D. A. McDonald, "The Relation of Pulsatile Pressure to Flow in Arteries", *J. Physiology*, vol. 127, pp. 533-552 (1955) and G. O. Barnett, "The Technique of Estimating Instantaneous Aortic Blood Velocity in Man from the Pressure Gradient", *American Heart Journal*, vol. 62, No. 3, pp. 359-366 (September 1961), and U.S. patent application Ser. No. 11/344,106 (Pub. No. 2006/0173366A1); Ser. No. 11/418,787 (Pub. No. 2006/0281668 A1); Ser. No. 10/591,742 (Pub. No. 2007/0197924); Ser. No. 11/453,848 (Pub. No. 2007/0004985) and Ser. No. 11/475,917 (Pub. No. 2007/0016085).

Although the methods disclosed in the noted references provide an effective means of determining pulse wave velocity, the methods are susceptible to significant error by virtue of the fact that the determinations of pulse transit time, which is a primary variable in pulse wave velocity equations and algorithms, fail to adequately account for the pre-ejection period ("PEP").

As discussed in detail herein, the error resulting from failing to account for PEP in a pulse transit time determination, which is carried into a pulse wave velocity determination, can vary, unpredictably in the range of 10-25% or more.

It would therefore be desirable to provide an improved method for accurately determining the pre-ejection period of a subject.

It would also be desirable to provide an improved method for determining pulse wave velocity that provides an accurate measure of pulse wave velocity by effectively accounting for the pre-ejection period.

As is well known in the art, there is diagnostic value and clinical utility for interventional therapy in either or both parameters, i.e. pre-ejection period and pulse wave velocity, as pre-ejection period is indicative mostly of the condition of the myocardium, whereas pulse wave velocity is mostly an indicator of the condition of the vasculature.

It is therefore an object of the present invention to provide improved methods for determining the pre-ejection period and pulse wave velocity that substantially reduce or eliminate the disadvantages and drawbacks associated with conventional methods and algorithms for determining the pre-ejection period and pulse wave velocity.

It is another object of the present invention to provide a method and algorithm for accurately determining the pre-ejection period.

It is another object of the present invention to provide a method and algorithm for determining pulse wave velocity that provides an accurate measure of pulse wave velocity by effectively accounting for the pre-ejection period.

It is another object of the present invention to provide a method for accurately determining cardiac output.

It is another object of the present invention to provide an improved method for assessing the status of the cardiovascular system.

SUMMARY OF THE INVENTION

In accordance with the above objects and those that will be mentioned and will become apparent below, in one embodiment of the invention, there is provided a method for determining a cardiac function associated with a subject, comprising the steps of (i) determining base anatomical characteristics associated with the subject, (ii) determining pulse delay to a first body site ($PD_{01}$) and a second body site ($PD_{02}$) as a function of the anatomical characteristics, wherein the distance via the arterial tree from the aortic valve to the first body site ($PD_{01}$) is different than the arterial tree distance from the aortic valve to the second body site ($PD_{02}$), (iii) determining pulse wave velocity between the first body site and the second body site ($PWV_{12}$), (iv) determining pulse wave velocity between the aortic valve and the first body site ($PWV_{01}$) as a function of $PWV_{12}$, and the anatomical characteristics, and (v) determining the pre-ejection period (PEP) as a function of $PD_{01}$ and $PWV_{01}$.

In one embodiment of the invention, the anatomical characteristics comprise the times required for a pressure wave to travel from the aortic valve to the first and second body sites, which are mathematically related to the arterial tree distances from the aortic valve to the first and second body sites, and the arterial tree distances from the aortic valve to the first and second body sites.

In another embodiment of the invention, the method for determining a cardiac function associated with a subject, comprises the steps of (i) determining base anatomical characteristics associated with a subject, (ii) determining pulse delay to a digit ($PD_{Digit}$) and an ear ($PD_{Ear}$) as a function of the anatomical characteristics, (iii) determining peripheral pulse transit time ($PTT_{Peripheral}$) as a function of $PD_{Digit}$ and $PD_{Ear}$, (iv) determining peripheral pulse wave velocity ($PWV_{Peripheral}$) as a function of $PTT_{Peripheral}$ and the arterial distances from the aortic valve to the digit and ear, (v) determining aortic pulse wave velocity ($PWV_{Central}$) as a function of $PWV_{Peripheral}$ and a standard ratio of $PWV_{Peripheral}$ to $PWV_{Central}$, and determining the pre-ejection period (PEP) as a function of $PWV_{Central}$ and the arterial the distance from the aortic valve to the ear.

In one embodiment, the base anatomical characteristics comprise the times required for a pressure wave to travel from the aortic valve to the tip of the digit and a pressure wave to travel from the aortic valve to the ear, and distances from the second intercostal space to suprasternal notch, the suprasternal notch to the base of the right ear, the suprasternal notch to the tip of the digit, and the arterial distances from the aortic valve to the digit and ear.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
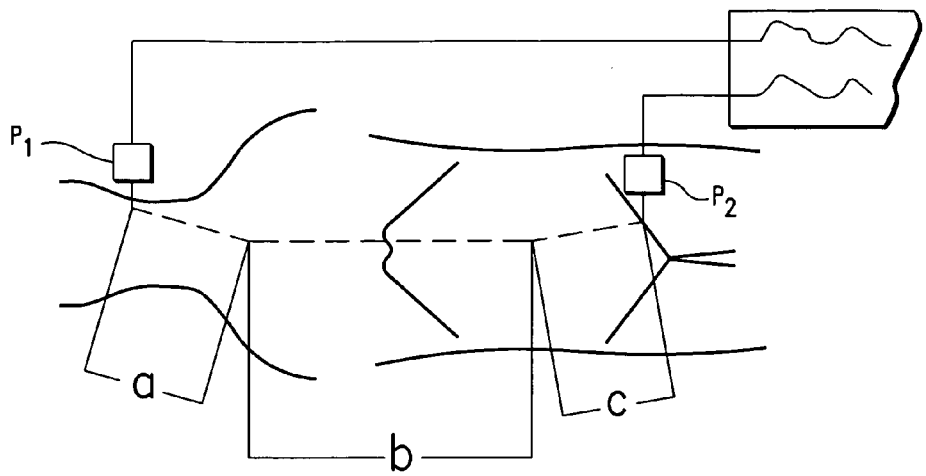
FIG. 1 is a schematic illustration of a conventional method for determining pulse wave velocity.
Figure 2:
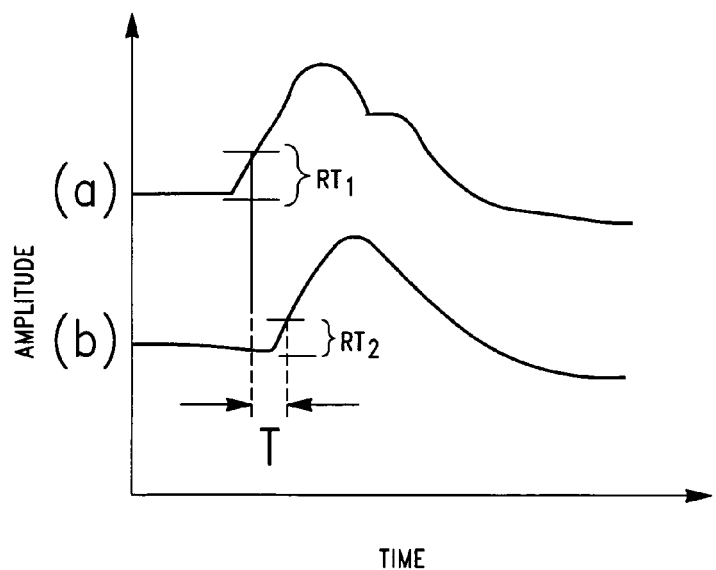
FIG. 2 is a graphical illustration of the pulse waveforms resulting from the pulse wave velocity method shown in FIG. 1.
Figure 3:
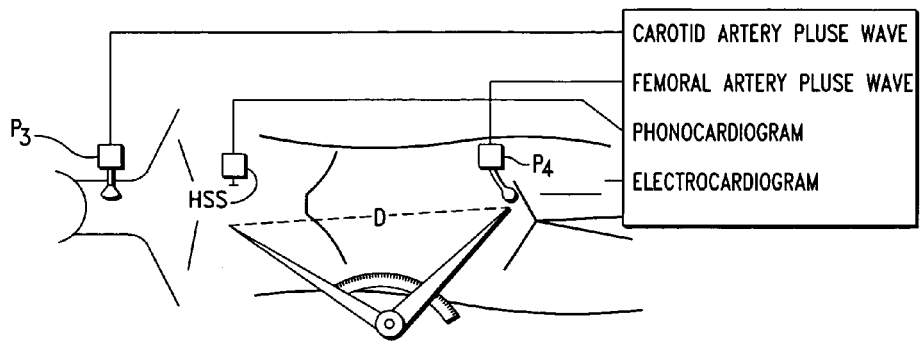
FIG. 3 is a schematic illustration of another conventional method for determining pulse wave velocity.
Figure 4:
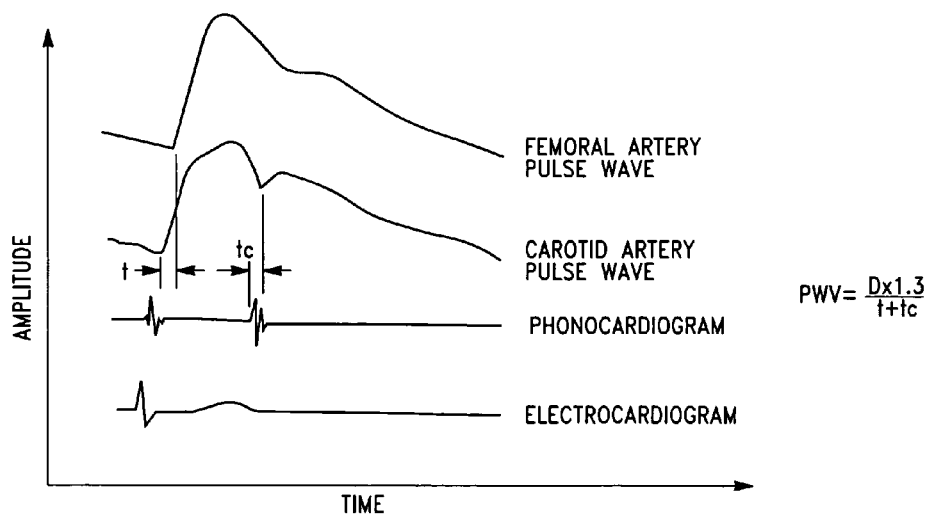
FIG. 4 is a graphical illustration of the pulse waveforms resulting from the pulse wave velocity method shown in FIG. 3.

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise.

DEFINITIONS

The term "signal", as used herein, is meant to mean and include, without limitation, an analog electrical waveform or a digital representation thereof, which is collected or transmitted by a biological or physiological sensor, such as a photoplethysmographic tissue probe or electrocardiogram.

The term "cardiac cycle", as used herein, is meant to mean and include, without limitation, a sequence of contractions (systole), which results in an increase in pressure and expelling of blood into the arteries, and relaxations (diastole), which results in a decrease in pressure and the filling of the heart chambers from the veins.

The term "pre-ejection period", as used herein, is meant to mean and include the time from the onset of the QRS to the opening of the aortic valve during the cardiac cycle.

The term "base anatomical characteristics", as used herein, means and includes, without limitation, the times required for a pressure wave to travel from the aortic valve to at least two body sites, and the arterial tree distances from the aortic valve to the body sites. The term "base anatomical characteristics" further means and includes physiological measurements provided via electrical measurements of the heart, electromagnetic absorption measurements through tissue, and/or determinations of body-part size changes as the result of blood flow (i.e. plethysmographic measurements).

The term "stroke volume", as used herein, is meant to mean and include, without limitation, a measure of volume pumped per beat, which is typically expressed as the volume of blood pumped from a ventricle of the heart in one beat.

The term "cardiac output", as used herein, is meant to mean and include, without limitation, a measure of the volume of blood pumped per time, which is typically expressed as the volume of blood ejected from the left side of the heart in one minute, in units of liters per minute (l/min).

The term "cardiac index", as used herein, is meant to mean and include, without limitation, a cardiodynamic measure based on the cardiac output. Cardiac index is typically expressed as the amount of blood the left ventricle ejects into the systemic circulation in one minute, divided by the body surface area ("BSA"), i.e. the total surface area of the human body. The cardiac index typically has units of $(l/min)/m^2$.

The terms "patient" and "subject", as used herein, is meant to mean and include humans and animals.

The present invention provides improved methods for determining the pre-ejection period and, hence, aortic pulse wave velocity that substantially reduces or eliminates the disadvantages and drawbacks associated with conventional methods and associated algorithms for determining the pre-ejection period and pulse wave velocity. As discussed in detail below, a key feature and, hence, advantage of the invention is that the methods and associated algorithms disclosed herein provide an accurate measure of pulse wave velocity by effectively accounting for the pre-ejection period.

As will be readily appreciated by one having ordinary skill in the art, accurate determination of pulse wave velocity is particularly beneficial in assessments of the cardiovascular system. Indeed, as discussed above, pulse wave velocity is often employed as an index of arterial elasticity and stiffness and, hence, in many instances, a predictor of coronary heart disease. Pulse wave velocity is also often employed to determine cardiac output and, hence, diagnostic information on cardiovascular performance based thereon.

Figure 5:
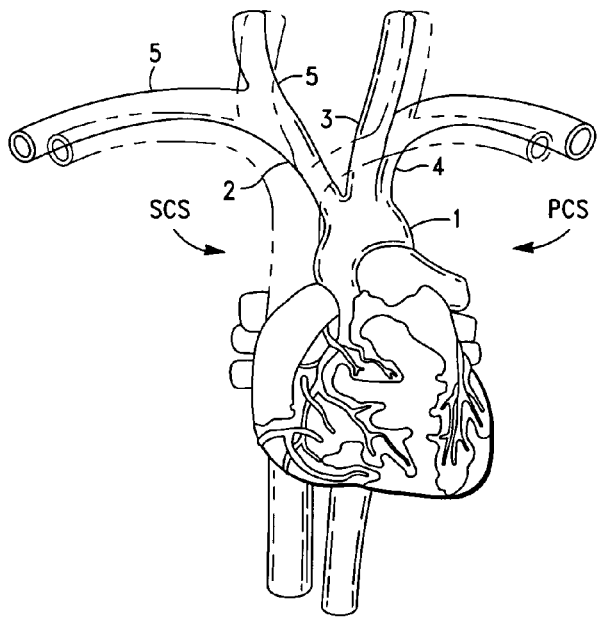
FIG. 5 is an illustration of a human heart, showing the pulmonary and systemic circulation sections.

Referring now to FIG. 5, there is shown an illustration of a human heart. As illustrated in FIG. 5, functionally, the heart is divided into two sides, i.e. right and left, or sections, i.e. pulmonary and systemic circulation sections. The right or pulmonary circulation section (designated "PCS") receives blood from the veins of the body and pumps it through the lungs. The left or systemic circulation section (designated "SCS") receives the blood from the lungs and pumps it to the body. The blood is then collected in the veins to be returned to the right side of the heart.

The arterial system begins at the aorta 1, to which the left ventricle of the heart pumps. The aorta 1 passes down (caudad) through the body, providing arterial branches to organs, and terminates as a bifurcation, i.e. creating the iliac arteries.

The first three branches of the aorta 1 are the brachiocephalic or innominate artery 2, the left (common) carotid artery 3, and the left subclavian artery 4. The brachiocephalic artery 2 branches into the right subclavian 5 and right (common) 6 carotid arteries. These arteries provide the blood supply for the head and upper extremities.

The brachiocephalic or innominate artery 2 is the first branch of the aorta 1. The innominate artery 2, in turn, branches into the right subclavian 5 and right carotid arteries 6. In contrast, the left subclavian 4 and left carotid arteries 3 originate directly off the aortic arch. Thus, the subclavian 4 and carotid arteries 3, as well as their branches, have different paths from their counterparts on the opposite side of the body.

Figure 6:
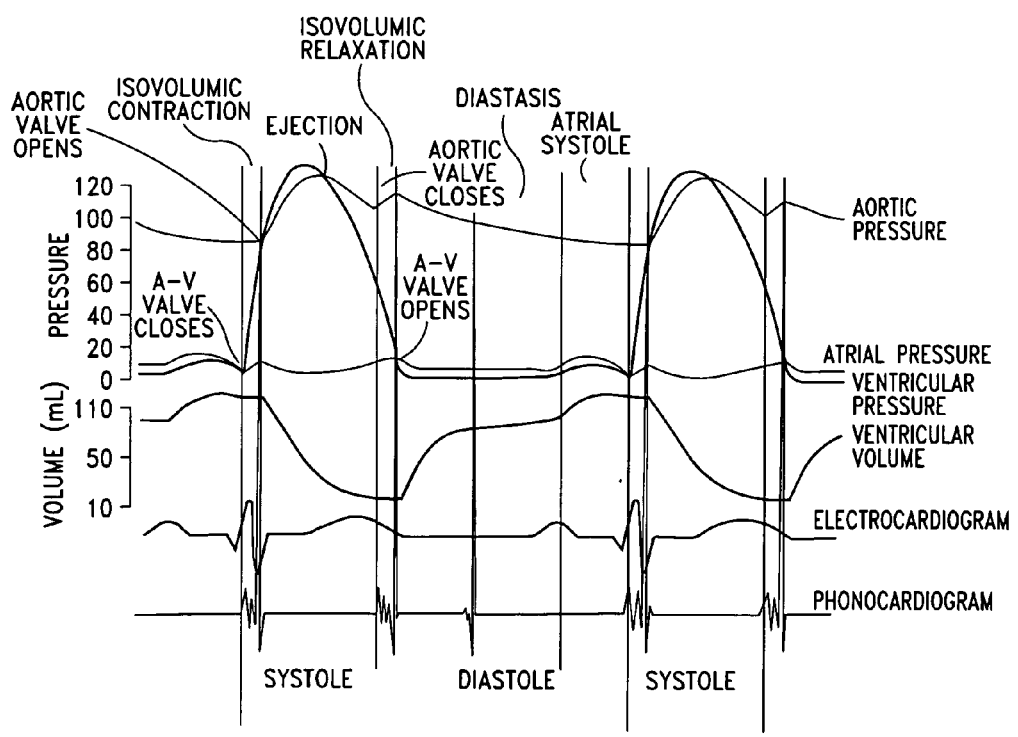
FIG. 6 is a graphical illustration of a cardiac cycle, showing cardiac events and changes in blood volume and pressure associated therewith.

Referring now to FIG. 6, there is shown a graphical illustration of a cardiac cycle (or heart beat), showing cardiac events and changes in blood volume and pressure associated therewith. As is well known in the art, a cardiac cycle is one of a sequence of contractions (systole), which, as illustrated in FIG. 6, results in an increase in pressure and expelling of blood into the arteries, and relaxations (diastole), which results in a decrease in pressure and the filling of the heart chambers from the veins.

The cardiac cycle is typically divided into distinct periods, i.e. diastole and systole, which are determined by electrical and mechanical events, i.e. diastolic and systolic events. The noted periods and events associated therewith are discussed in detail below.

Diastole is the period during which the filling of the ventricles occurs. Diastole is typically divided into four intervals: isovolumic relaxation, early diastolic filling, diastasis and atrial contraction.

At the end of systole, the semi-lunar valves shut and the ventricles relax, resulting in a fall in the intraventricular pressure. This is an active process, known as the period of isovolumic relaxation. Isovolumic relaxation ends when the pressure in the ventricles decreases to below that in the atria and the AV valves open (see FIG. 6).

At resting heart rates, the majority of the filling of the ventricles occurs during early diastolic filling. Early diastolic filling is often deemed a "passive" period, when the blood stored in the atrial "priming" chambers flows rapidly into the ventricles. Early diastolic filling ends when the elastic properties of the ventricle(s) prevent further filling and the pressure rises above that in the atria.

As illustrated in FIG. 6, diastasis is often the longest period in diastole. During diastasis, only a small amount of blood flows from the atria.

The second period of diastole, during which there is significant blood flow, is when the ventricles are actively filled by blood from atrial contraction. Atrial contraction includes a "pump-priming" action that increases the ventricular pressure immediately prior to systole.

Systole is the period during which the ventricles develop pressure to drive blood into the arteries. Systole is typically divided into three intervals: electromechanical delay, isovolumic contraction and the ejection period.

Electromechanical delay is the period of time taken for the electrical stimulus to result in activation of the ventricular muscle.

The period of isovolumic contraction is the period of time when the ventricles have begun to contract, but the volume of the chambers has not yet changed. It occurs immediately after the period of electromechanical delay, following electrical stimulation of the ventricles. During this period, intraventricular pressure increases until it is sufficient to open the semilunar valves and eject blood into the arteries (see FIG. 6).

The pre-ejection period ("PEP") typically includes both the electromechanical delay and isovolumic contraction.

The ejection period occurs when the semilunar valves have opened, and the ventricles eject the forward stroke volume into the systemic circulation, i.e. into the ascending aorta. There is a short period during which the velocity of blood flow accelerates to a peak, after which there is a gradual decline until the point at which the aortic pressure is sufficiently high to prevent further ejection of blood.

The ejection of blood into the ascending aorta acutely dilates the aortic wall and generates a pulse wave that propagates along the arterial tree at a finite speed. As discussed above, this propagation velocity, i.e. pulse wave velocity ("PWV"), constitutes an index of arterial distensibility or stiffness: the higher the velocity, the higher the rigidity of the vascular wall and the lower distensibility.

The pressure pulse generated by ventricular ejection is propagated throughout the arterial tree at a speed that is generally determined by the elastic and geometric properties of the arterial wall and the characteristics (e.g., density) of the contained fluid (i.e. blood). Since blood is an incompressible fluid and is contained in elastic conduits (i.e. arteries), the energy propagation occurs predominantly along the walls of the arteries and not through the incompressible blood. Thus, the properties of the arterial wall, its thickness, and the arterial lumen diameter are the major factors that influence pulse wave velocity.

Figure 7:
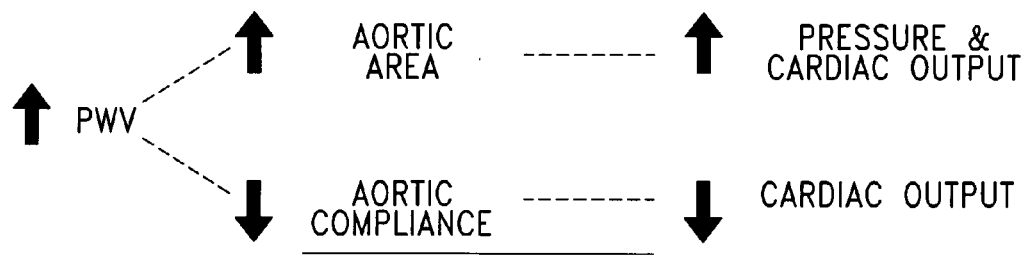
FIG. 7 is a schematic illustration reflecting the relationship between pulse wave velocity, aortic area, aortic compliance and cardiac output, according to the invention.

Referring now to FIG. 7, there is shown a schematic illustration reflecting the relationship between pulse wave velocity, aortic area, aortic compliance and cardiac output. As is known in the art, two significant factors that contribute to increases in pulse wave velocity are aortic cross-sectional area and, as discussed above, aortic compliance.

As illustrated in FIG. 7, pulse wave velocity and cardiac output will, in general, increase with increases in aortic cross-sectional area and without coincident changes in aortic compliance. A decrease in aortic compliance without a coincident change in aortic area will, in general, necessitate an increase in cardiac pressure and output to effectuate an increase in pulse wave velocity.

Figure 8:
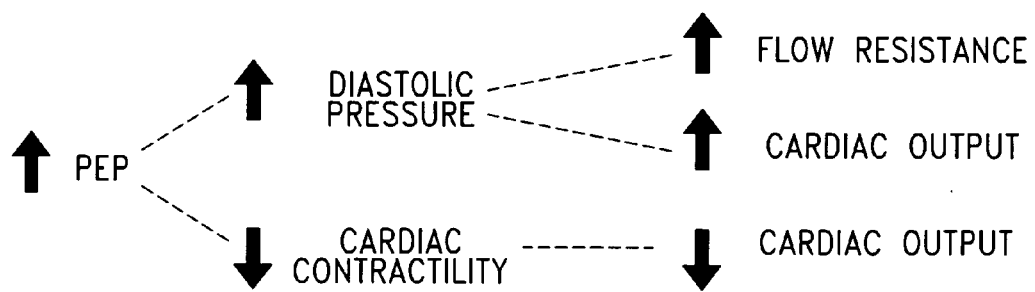
FIG. 8 is a schematic illustration reflecting the relationship between pre-ejection period, diastolic pressure, cardiac contractility and cardiac output, according to the invention.

Referring now to FIG. 8, there is shown a schematic illustration reflecting the relationship between pre-ejection period, diastolic pressure, cardiac contractility and cardiac output. As illustrated in FIG. 8, the pre-ejection period will, in general, increase with increases in end diastolic pressure and/or decreases in cardiac contractility. Decreases in cardiac contractility and/or cardiac output will also increase the pre-ejection period.

Figure 9:
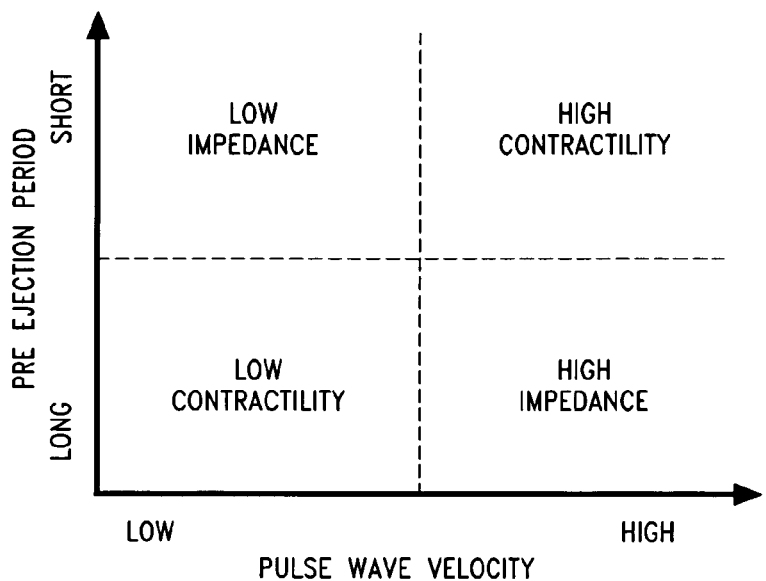
FIGS. 9 and 10 are schematic illustrations reflecting the relationship between pre-ejection period and pulse wave velocity, according to the invention.
Figure 10:
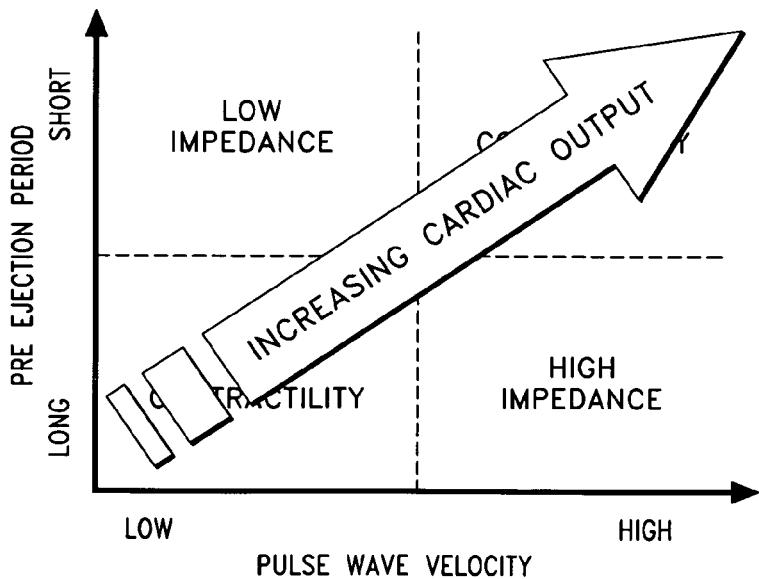
Figure 11:
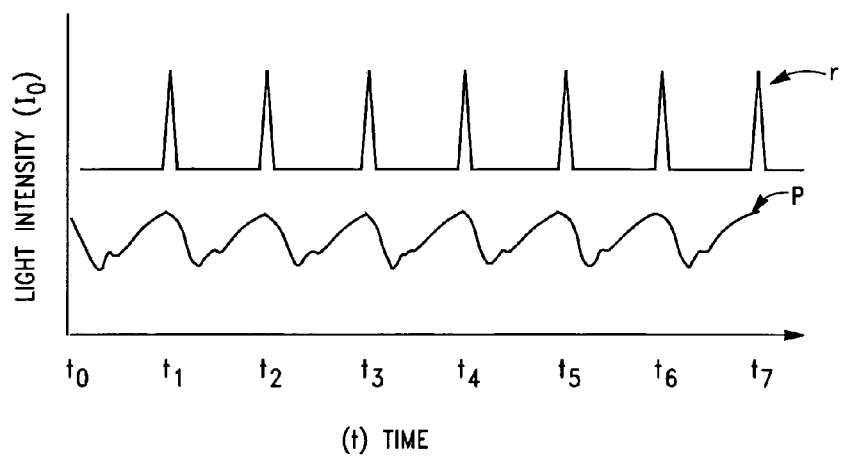
FIG. 11 is a graphical illustration of an R wave portion of an electrocardiogram waveform and the related plethysmographic waveform.

It is thus readily apparent that the combination of pre-ejection period and pulse wave velocity can provide a powerful indication of cardiac output and, hence, status of the cardiovascular system. Referring now to FIGS. 9 and 10, there are shown schematic illustrations reflecting the relationship between the pre-ejection period and pulse wave velocity, and the effects of cardiovascular factors on the relationship.

As illustrated in FIG. 9, when the pre-ejection period is relatively long and the pulse wave velocity is relatively low, it is reasonable to conclude that the cardiovascular system is operating under conditions of low contractility. Conversely, when the pre-ejection period is relatively short and the pulse wave velocity is relatively high, cardiac contractility must be enhanced.

As illustrated in FIG. 10, increased cardiac output (and pulse wave velocity) is realized with high contractility and low impedance. Increased cardiac output is also realized with a relatively short pre-ejection period and high pulse wave velocity.

As indicated, the present invention provides improved methods and algorithms for accurately determining (or estimating) the pre-ejection period and pulse wave velocity of a subject. According to the invention, the methods for determining the pre-ejection period and pulse wave velocity and the algorithms associated therewith are based on one or more physiological, non-invasive characteristics or measurements.

In at least one embodiment of the invention, the physiological measurements preferably include the times required for a pressure wave to travel from the aortic valve to at least two body sites, and the arterial tree distances from the aortic valve to the body sites.

In at least one embodiment of the invention, the physiological measurements preferably include the time from the onset of the QRS component to the initial arrival of the pressure wave to a desired location on the body, e.g., digit, nostrils, ear etc., more preferably, a first time from the onset of the QRS component to the initial arrival of a pressure wave at a point on the body that is proximate to the central circulation system and preferably close to the heart, such as the nose, earlobe, neck, etc., and a second time from the onset of the QRS component to the initial arrival of a pressure wave at a peripheral location or point on the body, such as a digit, hand, arm, etc., the arterial tree distances from the aortic valve to the designated central and peripheral locations on the body, and the distances between target locations on or within the body.

According to the invention, the physiological characteristics or measurements can be provided or acquired by various conventional means.

In some embodiments, one or more physiological measurements are provided via electrical measurements of the heart, electromagnetic radiation absorption measurements through tissue, and/or the determination of body-part size changes as the result of blood flow (i.e. plethysmographic measurements).

According to the invention, the electrical measurements of the heart can include, but are not limited to, ECG measurements. Electromagnetic radiation absorption measurements can include, but are not limited to, measurements of the absorption of light through the body, where the term "light" refers, without limitation, to electromagnetic radiation in the infrared or visible regions. Plethysmographic measurements can include, but are not limited to, electromagnetic radiation absorption measurements through portions of the body having measurable blood flow.

In one embodiment of the invention, an electrical measurement of the heart comprises the electric potential thereof, as measured by an electrocardiogram ("ECG"). Referring now to FIG. 7, there is shown a graphical illustration of an "R wave" portion of an ECG waveform (designated "r") and the related plethysmographic waveform (designated "p").

As is well known in the art, an ECG waveform, such as that shown in FIG. 6, comprises a complex waveform having several components that correspond to electrical heart activity. A significant component is the QRS component, which relates to ventricular heart contraction.

The R wave portion of the QRS component is typically the steepest wave therein, having the largest amplitude and slope, and is typically used to determine the onset of cardiovascular activity, i.e. initiation of isovolumic contraction (see FIG. 6). The arterial pulsed blood pulse flows mechanically and its appearance in any part of the body typically follows the R wave of the electrical heart activity by a determinable period of time that remains essentially constant for a given patient. See, e.g., Goodlin et al., "Systolic Time Intervals in the Fetus and Neonate", *Obstetrics and Gynecology*, vol. 39, No. 2 (February 1972) and U.S. Pat. No. 3,734,086.

In the noted embodiment, the ECG leads are preferably disposed on the body or torso at a location that facilitates determination of the onset of the QRS complex.

In another embodiment, one or more physiological measurements are provided via measurements of the blood flow through the body using one or more photoplethysmographic tissue probes. Preferably, each photoplethysmographic tissue probe is configured to communicate with or accept a body part, such as a finger or ear lobe, whereby one or more electromagnetic radiation emitters are disposed on one side of the tissue opposite one or more detectors to accept radiation from the emitters after passing through the tissue.

An example of a photoplethysmographic tissue probe is, for example, a pulse oximeter. Examples of suitable pulse oximeters (or optical probes) are disclosed in U.S. Pat. No. 6,537,225; which is incorporated by reference herein.

Derivation of the algorithm of the invention will now be discussed in detail. According to the invention, base physiological measurements or anatomical characteristics and pulse transit times (or pulse delays) to at least two selective sites on (or in) the body are initially determined. In a preferred embodiment of the invention, discussed in detail below, the pulse transit times include two pertinent times, i.e. the times from the onset of the QRS component to the initial arrival of a pressure wave (i) at a point proximate to the central circulation system and preferably close to the heart, such as the nose, earlobe, neck, upper chest, shoulder, etc., and (ii) at a peripheral point on the body, such as a digit, hand, arm, leg, etc (see FIG. 12).

In one embodiment of the invention, the following pulse transit times and distances (referred to herein as "anatomical characteristics") are initially determined: (i) the times required for a pressure wave to travel from the aortic valve to first and second sites on the body, and (ii) the distances via the arterial tree from the aortic valve to the first and second body sites; the noted arterial tree distances being different.

According to the invention, the pulse delays to the first body site ($PD_{01}$) and second body site ($PD_{02}$) can be represented by and, hence, determined from the following equations:

$$PD_{01} = PEP + PTT_{01} \qquad \text{Eq. 1}$$

$$PD_{02} = PEP + PTT_{02} = PEP + PTT_{01} + (PTT_{02} - PTT_{01}) \qquad \text{Eq. 2}$$

where:
PEP=the pre-ejection period, i.e. the time from the onset of the QRS component to the opening of the aortic valve during the cardiac cycle;
$PTT_{01}$=the time required for a pressure wave to travel from the aortic valve to the first body site; and
$PTT_{02}$=the time required for a pressure wave to travel from the aortic valve to the second body site.

In view of Equations 1 and 2, above, the average pulse wave velocity within the region from the first body site ($PD_{01}$) to the second body site ($PD_{02}$) (hereinafter denoted "$PWV_{12}$"), can be determined from the following equation:

$$PWV_{12} = \frac{D_{02} - D_{01}}{PTT_{02} - PTT_{01}} \qquad \text{Eq. 3}$$

$$= \frac{D_{02} - D_{01}}{(PD_{02} - PEP) - (PD_{01} - PEP)}$$

$$= \frac{D_{02} - D_{01}}{PD_{02} - PD_{01}}$$

where:
$D_{01}$=the arterial tree distance from the aortic valve to the first body site; and
$D_{02}$=the arterial tree distance from the aortic valve to the second body site.

As will be appreciated by one having ordinary skill in the art, although the pulse wave velocity in one segment of the arterial tree may not match the pulse wave velocity in another segment of the aortic tree, a relationship can exist, whereby $$PWV_{01} = f(PWV_{12}, \text{Patient}). \qquad \text{Eq. 4}$$

where $PWV_{01}$ represents aortic pulse wave velocity.

By way of example, McDonald, et al., *Blood Flow in Arteries, Theoretical Experimental and Clinical Principles*, (4$^{th}$ edition, 1998) provides that an age dependent relationship, i.e. $\alpha_{age}$, exists between aortic and peripheral pulse wave velocity, whereby $$PWV_{01} = PWV_{12} * \alpha_{age}. \qquad \text{Eq. 5}$$

In one embodiment, the pre-ejection period (PEP) is thus determined using the relationship shown in Equation 4 and according to the following equations:

$$PEP = PD_{01} - PTT_{01} \qquad \text{Eq. 6}$$

where:

$$PTT_{01} = \frac{D_{01}}{PWV_{01}} \qquad \text{Eq. 7}$$

$$= \frac{D_{01}}{f(PWV_{12}, \text{Patient})}$$

$$= \frac{D_{01}}{f\left(\frac{D_{02} - D_{01}}{PTT_{02} - PTT_{01}}, \text{Patient}\right)}.$$

Thus, $$PEP = PD_{01} - \frac{D_{01}}{f\left(\frac{D_{02} - D_{01}}{PTT_{02} - PTT_{01}}, \text{Patient}\right)}.$$

In a simplified case where $PWV_{01} = PWV_{12} * \alpha_{age}$, PEP can be determined as follows:

$$PEP = PD_{01} - \frac{D_{01}}{PWV_{12} * \alpha_{age}} \qquad \text{Eq. 8}$$

$$= PD_{01} - \frac{D_{01}}{\frac{D_{02} - D_{01}}{PD_{02} - PD_{01}} * \alpha_{age}}$$

$$= PD_{01} - \frac{(PD_{02} - PD_{01}) * D_{01}}{(D_{02} - D_{01}) * \alpha_{age}}$$

According to the invention, the derived PEP can then be employed as a factor (or variable) in known PWV algorithms (or equations) to enhance the determination of PWV. By way of example, in a simplified case where $$PWV_{01} = \frac{D_{01}}{PD_{01}}, \qquad \text{Eq. 9}$$

a more accurate determination of $PWV_{01}$ can be provided by accounting for PEP, as derived herein, i.e.

$$PWV_{01} = \frac{D_{01}}{PD_{01} - PEP}.\qquad\text{Eq. 10}$$

According to the invention, the first and second body sites in the embodiment described above need not be located on the same arterial tree, but rather can be viewed from the perspective of relative distance(s) down a lumped arterial tree.

Further, the accuracy of the measurements and, hence, cardiac determinations made therefrom can be enhanced by having the first body site disposed proximate the aortic valve and/or increasing the special distance (or separation) between the first and second body sites.

Figure 12:
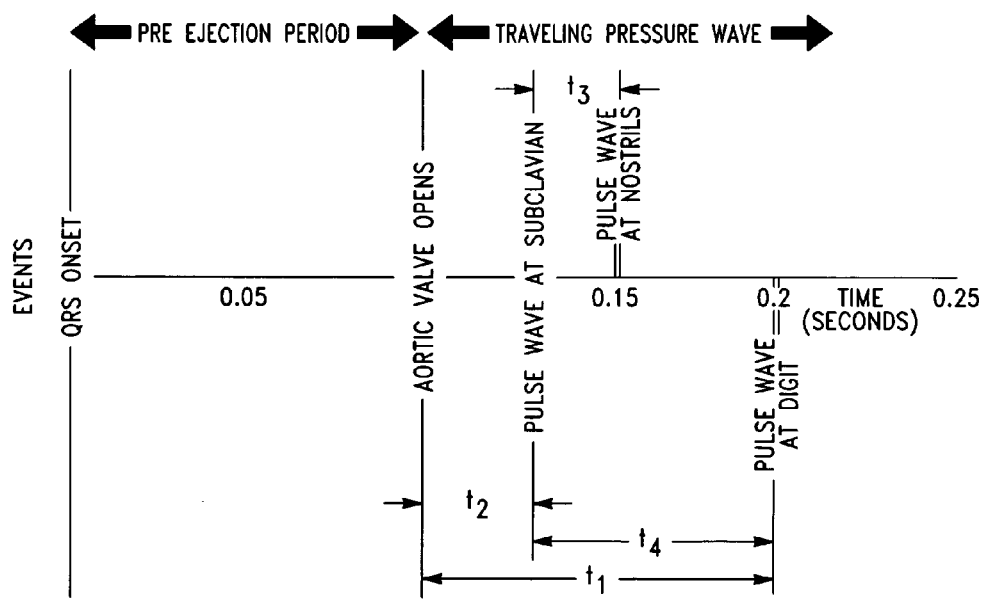
FIG. 12 is a schematic illustration of a pre-ejection period and the pulse wave propagation thereafter.

Referring to FIG. 12, in another embodiment of the invention, the following pulse transit times and distances are initially determined: (i) the times required for a pressure wave to travel from the aortic valve to the tip of a designated digit, and a pressure wave to travel from the aortic valve to a target location on the face (e.g., nose or earlobe), and (ii) the distances from the second intercostal space to suprasternal notch ("$D_{0x}$"), suprasternal notch to base of right ear ("$D_{x1}$"), and suprasternal notch to tip of a designated digit ("$D_{x2}$").

As will be appreciated by one having ordinary skill in the art, the foregoing is based on the anatomically correct assumption that the second intercostal space closely aligns anatomically with the aortic valve and the beginning of blood flow wave morphology. Measurements from the suprasternal notch are also easiest to obtain from subjects. Further, the differential between the right ear and left index finger extended right angle from the chest wall provides transmission measurements correlated to pulse transit time ("PTT") and other cardiac variables associated with cardiac output ("CO").

It is, however, understood that any mathematical relationship for estimating PEP and/or PWV, including the improved methods discussed herein, is limited by the relationship of physical distances in a population of individuals.

According to the invention, the distances from the second intercostal space to suprasternal notch ("$D_{0x}$"), suprasternal notch to base of right ear ("$D_{x1}$"), and suprasternal notch to tip of a designated digit ("$D_{x2}$"), can be measured directly, or approximated using basic demographic norms, such as the following:

$$D_{0x}(\text{women}) = 0.058\frac{\text{cm}}{\text{in}} \times Height_{in} + 2.79_{cm}\qquad\text{Eq. 11}$$

$$D_{0x}(\text{men}) = 0.058\frac{\text{cm}}{\text{in}} \times Height_{in} + 3.59_{cm}\qquad\text{Eq. 12}$$

$$D_{x1}(\text{women}) = -0.038\frac{\text{cm}}{\text{yrs}} \times Age_{yrs} + 17.09_{cm}\qquad\text{Eq. 13}$$

$$D_{x1}(\text{men}) = -0.038\frac{\text{cm}}{\text{yrs}} \times Age_{yrs} + 18.75_{cm}\qquad\text{Eq. 14}$$

$$D_{x2} = 1.1834\frac{\text{cm}}{\text{in}} \times Height_{in} + 0.0237\frac{\text{cm}}{\text{kg}} \times Weight_{kg} + 5.38_{cm}\qquad\text{Eq. 15}$$

Further, $$D_{01} = D_{0x} + D_{x1}\ \text{and}\qquad\text{Eq. 17}$$

$$D_{02} = D_{0x} + D_{x2}\qquad\text{Eq. 18}$$

where:
$D_{01}$=the arterial tree distance from the aortic valve to the ear; and
$D_{02}$=the arterial tree distance from the aortic valve to the digit.

The above referenced anatomical distances (as well as other anatomical distances and relationships) can also be determined via the relationships and equations set forth in Co-pending application Ser. No. 11/700,328, filed Jan. 30, 2007, which is incorporated herein in its entirety.

In accordance with one embodiment of the invention, the time for a pressure wave to travel from the aortic valve, i.e. the onset of the QRS component, to a peripheral location on the body (in this instance a designated digit) "$PD_{Digit}$", and the time for a pressure wave to travel from the aortic valve to the initial arrival of a pressure wave at a point proximate to the central circulation system and close to the heart (in this instance a target location on the ear) "$PD_{ear}$" are preferably determined from the following equations:

$$PD_{Digit}=PEP+PTT_{Digit}=PEP+PTT_{Ear}+PTT_{Digit}\qquad\text{Eq. 19}$$

$$PD_{Ear}=PEP+PTT_{Ear}\qquad\text{Eq. 20}$$

where:
$PTT_{Digit}=PTT_{02}$=the time required for a pressure wave to travel from the aortic valve to the digit;
$PTT_{Ear}=PTT_{01}$=the time required for a pressure wave to travel from the aortic valve to the ear; and
PEP=the pre-ejection period, i.e. the time from the onset of the QRS to the opening of the aortic valve during the cardiac cycle.

While other sites proximate the central circulation system, such as skin on the side of the neck, or cheek or upper chest or shoulder or forehead are useful and, hence, can be employed within the scope of the invention, the preferred and most readily accessible sites are the nose, such as the bridge or nostrils, and ear, particularly the earlobe.

By combining Equations 19 and 20 above, PEP can be eliminated from the equations, i.e.

$$PTT_{Peripheral}=PD_{Digit}-PD_{Ear}=PTT_{Digit}-PTT_{Ear}\qquad\text{Eq. 21}$$

where:
$PTT_{Digit}=D_{02}/PWV_{Digit}$;
$PTT_{Ear}=D_{01}/PWV_{Central}$; and
$PTT_{Peripheral}$=the time required for a pressure wave to travel down the arterial tree a distance equivalent to the portion of the tree for the ear to digit, respectively, i.e.

$$PTT_{02}-PTT_{01}\ \text{or}\ PTT_{Digit}-PTT_{Ear}=D_{12}/PWV_{Peripheral}.$$

Assuming that the pulse wave velocities in different body segments are related via patient demographics, central pulse wave velocity, $PWV_{Central}$, can be determined as follows:

$$PWV_{Central}=\alpha_v \times PWV_{Peripheral}\qquad\text{Eq. 22}$$

where:
$\alpha_v$=the standard ratio of peripheral PWV to central PWV, i.e. $\alpha_v=PWV_{Central}/PWV_{Peripheral}$, wherein aortic PWV is a major component.

In one embodiment of the invention, $$\alpha_v = \frac{500\,\text{cm/sec}}{730\,\text{cm/sec}} = 0.68.$$

See McDonald, et al., *Blood Flow in Arteries, Theoretical Experimental and Clinical Principles*, p. 92 (4th edition, 1998).

In another embodiment, $\alpha_v$ is be adjusted as a function age, i.e.

$$\alpha_v = \frac{553 \frac{cm}{sec} + ((Age_{yrs} - 18_{yrs}) \times 6.10 \frac{cm}{sec}/yrs)}{817 \frac{cm}{sec} + ((Age_{yrs} - 18_{yrs}) \times 0.10 \frac{cm}{sec}/yrs)} \quad \text{Eq. 23}$$

As is well known in the art, aortic compliance decreases with advanced age. Thus, as reflected in Equation 23, $\alpha_v$ tends toward unity in the elderly.

Equation 21 can then be re-written as follows:

$$D_{12}/PWV_{Peripheral} = PTT_{Peripheral} = PD_{Digit} - PD_{Ear} \quad \text{Eq. 24}$$

According to the invention, $PWV_{Peripheral}$ can then be determined through physiological measurements, i.e. $PD_{Digit}$ and $PD_{Ear}$, and demographic driven assumptions, by rewriting Equation 22, i.e.

$$PWV_{Peripheral} = \frac{D_{12}}{(PD_{Digit} - PD_{Ear})} \quad \text{Eq. 25}$$

where D represents the difference between the arterial tree distances from the aortic valve to the digit and ear.

Combining Equations 22 and 25 yields an estimate aortic pulse wave velocity, i.e.

$$PWV_{Central} = \alpha_v \times PWV_{Peripheral} = \frac{D_{12} \times \alpha_v}{(PD_{Digit} - PD_{Ear})} \quad \text{Eq. 26}$$

It should be noted that the estimate of $PWV_{Central}$ in Equation 26 is independent of PEP.

Now that PWV is determined in various branches of the arterial tree, PEP can be determined using Equations 7 or 8 as a basis, i.e.

$$PEP = PD_{Ear} - \frac{D_{01}}{PWV_{Peripheral} * \alpha_v} \quad \text{Eq. 27}$$

$$= \frac{D_{01}}{\frac{D_{02} - D_{01}}{PD_{Digit} - PD_{Ear}} * \alpha_v}$$

$$= \frac{(PD_{Digit} - PD_{Ear}) * D_{01}}{(D_{02} - D_{01}) * \alpha_v}$$

The analytical algorithm of the invention thus provides an effective and accurate means for determining the pre-ejection period and accounting for (i.e. correcting for) the pre-ejection period in pulse wave velocity determinations. As indicated above, the error resulting from failing to account for the pre-ejection period can vary, unpredictably in the range of 10-25% or more. By virtue of the methods and algorithm of the invention, the noted error can be substantially reduced or eliminated.

According to another embodiment of the invention, the mathematical relationships between PEP and PWV and the measured variables of pulse delays, pulse pressures, weight, age, height, and gender can be determined implicitly by means of multivariate calibration on data from a number of individuals.

EXAMPLES

The following examples are provided to enable those skilled in the art to more clearly understand and practice the present invention. They should not be considered as limiting the scope of the invention, but merely as being illustrated as representative thereof.

Example 1

An elderly female patient is presented with the following:
(i) age: 92 years;
(ii) height: 62 inches;
(iii) weight: 79 Kg: and
(iv) arterial hypertension (systolic pressure=151 mmHg and diastolic pressure=89 mmHg).

The following basic distances were employed:

$$D_{01} = D_{0x} + D_{x1} = 8.00 \text{ cm} + 13.00 \text{ cm} = 21 \text{ cm}; \quad \text{(i)}$$

$$D_{02} = D_{0x} + D_{x2} = 8.00 \text{ cm} + 74.00 \text{ cm} = 82 \text{ cm}; \text{ and} \quad \text{(ii)}$$

$$D_{12} = D_{02} - D_{01} = 82.00 \text{ cm} - 21.00 \text{ cm} = 61 \text{ cm}. \quad \text{(iii)}$$

The following measurements were also determined:
(i) $D_{0x} = 8.00$ cm;
(ii) $D_{x1} = 13.00$ cm; and
(iii) $D_{x2} = 74.00$ cm.

From measured patient data the following was also provided:
(i) $PD_{Digit} = 0.1984$ seconds; and
(ii) $PD_{Ear} = 0.1627$ seconds.

Using a value of 0.88 for ratio parameter $\alpha_v$, pulse wave velocity (PWV) and pre-ejection period (PEP) is then determined, as set forth above, i.e.

$$PWV_{Central} = \alpha_v \times PWV_{Peripheral}$$

$$= \frac{D_{12} \times \alpha_v}{(PD_{Digit} - PD_{Ear})}$$

$$= \frac{61 \text{ cm} \times 0.88}{(0.1984_{sec} - 0.1627_{sec})}$$

$$= 1627 \frac{cm}{sec}$$

$$PEP = PD_{Ear} - \frac{(PD_{Digit} - PD_{Ear}) * D_{01}}{(D_{02} - D_{01}) * \alpha_{age}}$$

$$= 0.1627_{sec} - \frac{(0.1984_{sec} - 0.1627_{sec}) * 21_{cm}}{61_{cm} * 0.88}$$

$$= 0.148 \text{ sec}$$

Example 2

A young normotensive female patient is presented with the following:
(i) age: 42 years;
(ii) height: 63 inches;
(iii) weight: 79 Kg: and
(v) arterial hypertension (systolic pressure=130 mmHg and diastolic pressure=7 mmHg).

The following basic distances were employed:

$$D_{01} = D_{0x} + D_{x1} = 6.35 \text{ cm} + 13.97 \text{ cm} = 20.32 \text{ cm}; \quad (i)$$

$$D_{02} = D_{0x} + D_{x2} = 6.35 \text{ cm} + 80.01 \text{ cm} = 86.36 \text{ cm}; \text{ and} \quad (ii)$$

$$D_{12} = D_{02} - D_{01} = 86.36 \text{ cm} - 20.32 \text{ cm} = 66.04 \text{ cm}. \quad (iii)$$

The following measurements were also determined:
(i) $D_1 = 6.35$ cm;
(ii) $D_2 = 13.97$ cm; and
(iii) $D_4 = 80.01$ cm.

From measured patient data the following was also provided:
(i) PulseDelay$_{Digit}$ = 0.1942 seconds; and
(ii) PulseDelay$_{Facial}$ = 0.1472 seconds.

Using a value of 0.88 for ratio parameter $\alpha_v$, pulse wave velocity (PWV) and pre-ejection period (PEP) is then determined, as set forth above, i.e.

$$\begin{aligned} PWV_{Central} &= \alpha_v \times PWV_{Peripheral} \\ &= \frac{D_{12} \times \alpha_v}{(PD_{Digit} - PD_{Ear})} \\ &= \frac{66.04 \text{ cm} \times 0.88}{(0.1942_{sec} - 0.1472_{sec})} \\ &= 955 \frac{\text{cm}}{\text{sec}} \end{aligned}$$

$$\begin{aligned} PEP &= PD_{Ear} - \frac{(PD_{Digit} - PD_{Ear}) * D_{01}}{(D_{02} - D_{01}) * \alpha_{age}} \\ &= 0.1472_{sec} - \frac{(0.1942_{sec} - 0.1472_{sec}) * 20.32_{cm}}{66.04_{cm} * 0.88} \\ &= 0.131 \text{ sec} \end{aligned}$$

In the two previous examples, PD$_{digit}$ is within 0.0042 seconds of each other. Without additional information, one may mistakenly conclude that PWV for both patients was substantially equivalent. Only when additional information, i.e. PD$_{Ear}$, is available, will the underlying components, PWP and PEP be separable and their physiologic importance utilized.

Without departing from the spirit and scope of this invention, one having ordinary skill in the art can make various changes and modifications to the invention to adapt it to various usages and conditions. As such, these changes and modifications are properly, equitably, and intended to be, within the full range of equivalence of the following claims.

What is claimed is:

1. A method for determining a cardiac function associated with a subject, comprising the steps of:
   determining base anatomical characteristics associated with the subject;
   determining pulse delay to a first body site (PD$_{01}$) and a second body site (PD$_{02}$) as a function of the anatomical characteristics, wherein the distance via the arterial tree from the aortic valve to said first body site (PD$_{01}$) is different than the arterial tree distance from said aortic valve to said second body site (PD$_{02}$);
   determining pulse wave velocity between said first body site and said second body site (PWV$_{12}$);
   determining pulse wave velocity between said aortic valve and said first body site (PWV$_{01}$) as a function of said PWV$_{12}$, and said anatomical characteristics; and
   determining, using a non-transitory computer readable medium, the pre-ejection period (PEP) as a function of said PD$_{01}$ and PWV$_{01}$.

2. The method of claim 1, wherein said anatomical characteristics comprise the times required for a pressure wave to travel from said aortic valve to said first and second body sites, and said arterial tree distances from said aortic valve to said first and second body sites.

3. The method of claim 1, wherein said pulse delay to said first body site (PD$_{01}$) and said second body site (PD$_{02}$) is determined as a function of said anatomical characteristics and according to the following equations $$PD_{01} = PEP + PTT_{01}$$

and $$PD_{02} = PEP + PTT_{02} = PEP + PTT_{01} + (PTT_{02} - PTT_{01}),$$

wherein PEP represents the pre-ejection period, PTT$_{01}$ represents the time required for a pressure wave to travel from the aortic valve to the first body site, PTT$_{02}$ represents the time required for a pressure wave to travel from the aortic valve to the second body site, and (PTT$_{02}$−PTT$_{01}$) represents the time required for a pressure wave to travel from the first body site to the second body site.

4. The method of claim 3, wherein said pulse wave velocity within said arterial region between said first body site and said second body site (PWV$_{12}$) is determined according to the following equation $$\begin{aligned} PWV_{12} &= \frac{D_{02} - D_{01}}{PTT_{02} - PTT_{01}} \\ &= \frac{D_{02} - D_{01}}{(PD_{02} - PEP) - (PD_{01} - PEP)} \\ &= \frac{D_{02} - D_{01}}{PD_{02} - PD_{01}}, \end{aligned}$$

wherein D$_{01}$ represents said arterial tree distance from said aortic valve to said first body site, and D$_{02}$ represents said arterial tree distance from said aortic valve to said second body site.

5. The method of claim 1, wherein said pulse wave velocity between said aortic valve and said first body site (PWV$_{01}$) is determined according to the following equation $$PWV_{01} = f(PWV_{12}, \text{Patient})$$

wherein f(PWV$_{12}$,Patient) represents a patient dependent relationship between said pulse wave velocity between said aortic valve and said first body site and said pulse wave velocity between said first body site and said second body site.

6. The method of claim 1, wherein said pulse wave velocity between said aortic valve and said first body site (PWV$_{01}$) is determined according to the following equation $$PWV_{01} = PWV_{12} * \alpha_{age}$$

wherein $\alpha_{age}$ represents an age dependant relationship between aortic pulse wave velocity and peripheral pulse wave velocity.

7. The method of claim 6, wherein said age dependant relationship between said aortic pulse wave velocity and said peripheral pulse wave velocity comprises a ratio of said aortic pulse wave velocity to said peripheral pulse wave velocity.

8. The method of claim 5, wherein said pre-ejection period (PEP) is determined according to the following equation $$PEP = PD_{01} + PTT_{01},$$

wherein $$PTT_{01} = \frac{D_{01}}{PWV_{01}}$$
$$= \frac{D_{01}}{f(PWV_{12}, \text{Patient})}$$
$$= \frac{D_{01}}{f\left(\frac{D_{02} - D_{01}}{PTT_{02} - PTT_{01}}, \text{Patient}\right)}.$$

9. The method of claim 7, wherein said PEP is determined according to the following equation $$PEP = PD_{01} - \frac{D_{01}}{PWV_{12} * \alpha_{age}}$$
$$= PD_{01} - \frac{D_{01}}{\frac{D_{02} - D_{01}}{PD_{02} - PD_{01}} * \alpha_{age}}$$
$$= PD_{01} - \frac{(PD_{02} - PD_{01}) * D_{01}}{(D_{02} - D_{01}) * \alpha_{age}}.$$

10. A method of determining a cardiac function associated with a subject, comprising the steps of:
   determining base anatomical characteristics associated with the subject;
   determining pulse delay to a digit ($PD_{Digit}$) and an ear ($PD_{Ear}$) as a function of said anatomical characteristics;
   determining peripheral pulse transit time ($PTT_{Peripheral}$) as a function of said $PD_{Digit}$ and $PD_{Ear}$;
   determining peripheral pulse wave velocity ($PWV_{Peripheral}$) as a function of said $PTT_{Peripheral}$ and the arterial distances from the aortic valve to said digit and ear;
   determining central pulse wave velocity ($PWV_{Central}$) as a function of said $PTT_{Peripheral}$ and a standard ratio of $PWV_{Peripheral}$ to $PWV_{Central}$ ($\alpha_v$); and
   determining, using a non-transitory computer readable medium, the pre-ejection period (PEP) as a function of $PWV_{Central}$ and the arterial said distance from said aortic valve to said ear.

11. The method of claim 10, wherein said base anatomical characteristics are selected from the group comprising the times required for a pressure wave to travel from the aortic valve to the tip of said digit and a pressure wave to travel from said aortic valve to said ear, and distances from the second intercostal space to suprasternal notch, said suprasternal notch to the base of the right ear, said suprasternal notch to the tip of said digit, and the arterial distances from said aortic valve to said digit and ear.

12. The method of claim 11, wherein said pulse delay to said digit ($PD_{Digit}$) and ear ($PD_{Ear}$) on said subject's body is determined as a function of said anatomical characteristics and according to the following equations $$PD_{Digit} = PEP + PTT_{Digit} = PEP + PTT_{Ear} + PTT_{Digit}$$

and $$PD_{Ear} = PEP + PTT_{Ear},$$

wherein PEP represents said pre-ejection period, $PTT_{Digit}$ represents said time required for a pressure wave to travel from said aortic valve to said digit, and $PTT_{Ear}$ represents said time required for a pressure wave to travel from said aortic valve to said ear.

13. The method of claim 12, wherein said $PTT_{Peripheral}$ is determined according to the following equation $$PTT_{Peripheral} = PD_{Digit} - PD_{Ear} = PTT_{Digit} - PTT_{Ear}.$$

14. The method of claim 13, wherein said peripheral pulse wave velocity ($PWV_{Peripheral}$) is determined according to the following equation $$PWV_{Peripheral} = \frac{D_{12}}{(PD_{Digit} - PD_{Ear})},$$

wherein $D_{12}$ represents the difference between the arterial tree distances from said aortic valve to said digit and ear.

15. The method of claim 14, wherein said central pulse wave velocity ($PWV_{Central}$) is determined according to the following equation $$PWV_{Central} = \alpha_v \times PWV_{Peripheral} = \frac{D_{12} \times \alpha_v}{(PD_{Digit} - PD_{Ear})}.$$

16. The method of claim 15, wherein said $\alpha_v$=0.68.

17. The method of claim 15, wherein said $\alpha_v$ is adjusted as a function of age according to the following equation $$\alpha_v = \frac{553 \frac{cm}{sec} + \left((Age_{yrs} - 18_{yrs}) \times 6.10 \frac{cm}{sec}/yrs\right)}{817 \frac{cm}{sec} + \left((Age_{yrs} - 18_{yrs}) \times 0.10 \frac{cm}{sec}/yrs\right)}.$$

18. The method of claim 15, wherein said PEP is determined according to the following equation $$PEP = PD_{Ear} - \frac{D_{01}}{PWV_{Peripheral} * \alpha_v}$$
$$= \frac{D_{01}}{\frac{D_{02} - D_{01}}{PD_{Digit} - PD_{Ear}} * \alpha_v}$$
$$= \frac{(PD_{Digit} - PD_{Ear}) * D_{01}}{(D_{02} - D_{01}) * \alpha_v}$$

wherein $D_{01}$ represents said arterial tree distance from said aortic valve to said ear, and $D_{02}$ represents said arterial tree distance from said aortic valve to said digit.

19. A method of determining pre-ejection period (PEP) using a non-transitory computer readable medium, comprising the step of determining PEP according to the following equation $$PEP = PD_{Ear} - \frac{D_{01}}{PWV_{Peripheral} * \alpha_v}$$
$$= \frac{D_{01}}{\frac{D_{02} - D_{01}}{PD_{Digit} - PD_{Ear}} * \alpha_v}$$
$$= \frac{(PD_{Digit} - PD_{Ear}) * D_{01}}{(D_{02} - D_{01}) * \alpha_v},$$

wherein $PD_{Ear}$ represents pulse delay to an ear, $PD_{Digit}$ represents pulse delay to a designated digit, $D_{01}$ represents arterial tree distance from the aortic valve to said ear, $D_{02}$ represents arterial tree distance from said aortic valve to said digit, $PWV_{Peripheral}$ represents peripheral pulse wave velocity, and $\alpha_v$ represents a standard ratio of $PWV_{Peripheral}$ to central pulse wave velocity ($PWV_{Central}$).

\* \* \* \* \*

UNITED STATES PATENT AND TRADEMARK OFFICE
CERTIFICATE OF CORRECTION

| | | |
|---|---|---|
| PATENT NO. | : 8,834,382 B2 | Page 1 of 1 |
| APPLICATION NO. | : 12/011122 | |
| DATED | : September 16, 2014 | |
| INVENTOR(S) | : Voss et al. | |

It is certified that error appears in the above-identified patent and that said Letters Patent is hereby corrected as shown below:

Title page of the Patent, Under the item Titled FOREIGN PATENT DOCUMENTS, the second document listed as "WO PCT/IL03/00586" should read: -- WO PCT/IL03/000586 --

In the Claims

Claim 10, Column 17, line 42, the text beginning with "the arterial said distance", should read -- the arterial distance --

Signed and Sealed this
Seventeenth Day of March, 2015

Michelle K. Lee
*Director of the United States Patent and Trademark Office*